United States Patent
Lesch et al.

(10) Patent No.: US 11,781,102 B2
(45) Date of Patent: Oct. 10, 2023

(54) LARGE-SCALE PEI-MEDIATED PLASMID TRANSFECTION

(71) Applicant: Trizell Ltd., Chinnor (GB)

(72) Inventors: Hanna P. Lesch, Kuopio (FI); Joonas Malinen, Kuopio (FI); Eevi Lipponen, Kuopio (FI); Anniina Valkama, Kuopio (FI); Hanna Leinonen, Kuopio (FI)

(73) Assignee: Trizell Ltd., West Drayton (GB)

( * ) Notice: Subject to any disclaimer, the term of this patent is extended or adjusted under 35 U.S.C. 154(b) by 1175 days.

(21) Appl. No.: 15/777,228

(22) PCT Filed: Apr. 25, 2017

(86) PCT No.: PCT/IB2017/001205
§ 371 (c)(1),
(2) Date: May 18, 2018

(87) PCT Pub. No.: WO2018/007873
PCT Pub. Date: Jan. 11, 2018

(65) Prior Publication Data
US 2020/0165557 A1     May 28, 2020

Related U.S. Application Data

(63) Continuation of application No. PCT/US2017/025681, filed on Apr. 3, 2017.

(60) Provisional application No. 62/322,651, filed on Apr. 14, 2016.

(51) Int. Cl.
| | |
|---|---|
| *C12M 1/00* | (2006.01) |
| *C12M 1/02* | (2006.01) |
| *C12P 21/02* | (2006.01) |
| *C12M 1/12* | (2006.01) |
| *C12N 15/86* | (2006.01) |
| *C12M 1/34* | (2006.01) |
| *C07K 14/005* | (2006.01) |

(52) U.S. Cl.
CPC ........... *C12M 29/18* (2013.01); *C07K 14/005* (2013.01); *C12M 1/02* (2013.01); *C12M 25/18* (2013.01); *C12M 29/10* (2013.01); *C12M 41/26* (2013.01); *C12M 41/46* (2013.01); *C12N 15/86* (2013.01); *C12P 21/02* (2013.01); *C12N 2740/15051* (2013.01)

(58) Field of Classification Search
CPC ........ C12M 29/18; C12M 1/02; C12M 25/18; C12M 29/10; C12M 41/26; C12M 41/46; C07K 14/005; C12P 21/02; C12N 15/86; C12N 2740/15051
See application file for complete search history.

(56) References Cited

U.S. PATENT DOCUMENTS

| | | | |
|---|---|---|---|
| 5,622,857 | A | 4/1997 | Goffe |
| 11,242,504 | B2 | 2/2022 | Valonen et al. |
| 11,261,416 | B2 | 3/2022 | Valonen et al. |
| 2002/0177215 | A1 | 11/2002 | Zhang et al. |
| 2005/0201983 | A1 | 9/2005 | Yla-Herttuala et al. |
| 2011/0189764 | A1 | 8/2011 | Starbard |
| 2014/0255994 | A1 | 9/2014 | Konstantinov et al. |
| 2014/0315294 | A1* | 10/2014 | Marceau ................. C12N 7/02 435/320.1 |
| 2017/0051309 | A1 | 2/2017 | Lesch et al. |
| 2019/0031998 | A1 | 1/2019 | Valonen et al. |
| 2019/0218495 | A1 | 7/2019 | Valonen et al. |
| 2022/0364036 | A1 | 11/2022 | Valonen et al. |

FOREIGN PATENT DOCUMENTS

| | | |
|---|---|---|
| EP | 0295567 A1 | 12/1988 |
| WO | WO-2005/095578 A1 | 10/2005 |
| WO | WO-2014/130864 A2 | 8/2014 |
| WO | WO-2016/048556 A1 | 3/2016 |
| WO | WO-2017/180341 A2 | 10/2017 |
| WO | WO-2018/007873 A1 | 1/2018 |

OTHER PUBLICATIONS

Kuroda, H., Kutner, R. H., Bazan, N. G., & Reiser, J. (2009). Simplified lentivirus vector production in protein-free media using polyethylenimine-mediated transfection. Journal of virological methods, 157(2), 113-121 (Year: 2009).*
Karolewski, B. A., Watson, D. J., Parente, M. K., & Wolfe, J. H. (2003). Comparison of transfection conditions for a lentivirus vector produced in large volumes. Human gene therapy, 14(14), 1287-1296 (Year: 2003).*
Ogris, M., Steinlein, P., Kursa, M., Mechtler, K., Kircheis, R., & Wagner, E. (1998). The size of DNA/transferrin-PEI complexes is an important factor for gene expression in cultured cells. Gene therapy, 5(10), 1425-1433 (Year: 1998).*
Sartorius "Biostat B" Retrieved from https://www.sartorius.com/download/34576/broch-biostat-b-sbi1513-e-1--data.pdf on Oct. 14, 2022 (Year: 2020).*
Ansorge, S. et al, Development of a scalable process for high-yield lentiviral vector production by transient transfection of HEK293 suspension cultures, Journal Of Gene Medicine, 11(10): 868-876 (2009).
Chahal, P. S, et al., Production of adeno-associated virus (AAV) serotypes by transient transfection of HEK293 cell suspension cultures for gene delivery, Journal of Virological Methods 196:163-173 (2014).

(Continued)

*Primary Examiner* — Robert J Yamasaki
*Assistant Examiner* — Trevor L Kane
(74) *Attorney, Agent, or Firm* — Choate, Hall & Stewart LLP; Rolando Medina; Nnamdi Edokobi

(57) ABSTRACT

We have found a way to make possible large-scale plasmid transfection using PEI to produce high titer viral vectors in fixed bed or adherent cell culture bioreactors by using PEI as a transfection agent, while avoiding formation of the PEI-plasmid precipitate which in prior art approaches clogged adherent bioreactor substrates. We have also found a way to improve PEI-based transfection by modifying how pH and $CO_2$ are managed during transfection.

8 Claims, 5 Drawing Sheets

(56) References Cited

OTHER PUBLICATIONS

Chiorini, J. A. et al., Cloning and characterization of adeno-associated virus type 5, Journal of Virology, 73(2):1309-1319 (1999).
Coleman, J. E. et al., Efficient large-scale production and concentration of HIV-I-based lentiviral vectors for use in vivo, Physiol Genomics, 12(3):221-228 (2003).
Cortin, V., et al., A. High-titer adenovirns vector production in 293S cell perfusion culture, Biotechnol Prog., 20(3):858-63 (2004).
Dormond, E., et al., From the first to the third generation adenoviral vector: what parameters are governing the production yield?, Biotechnol Adv., 27(2):133-44 (2009).
Ferreira ,T. B., Effect ofre feed strategies and non-ammoniagenic medium on adenovirns production at high cell densities, J. Biotechnol., 119(3):272-80 (2005).
Follenzi, A. and Naldini, L., Generation of HIV-I derived lentiviral vectors, Methods Enzymol., 346:454-465 (2002).
Geraerts, M., et al., Upscaling of lentiviral vector production by tangential flow filtration., J. Gene Med., 7:1299-1310 (2005).
ICELLis® 500 Bioreactor Revision E Controller, Pall Life Sciences, Instructions for Use, Handbook, 151 pages.
ICELLis® 500 Revision E Controller Instructions for Use, Handbook, Pall Life Sciences, 153 pages.
International Search Report for PCT/IB2017/001205, 6 pages (dated Nov. 29, 2017).
International Search Report for PCT/US2017/025681, 3 pages (dated Oct. 2, 2017).
Iyer P, et al., Comparison of manufacturing techniques for adenovirns production., Cytotechnology., 30:169-72 (1999).
Kamen A. and Henry, O., Development and optimization of an adenovirus production process., J Gene Med., 6 Suppl 1:S184-S192 (2004).
Karolewski, B. A. et al., Comparison of transfection conditions for a lentivirus vector produced in large volumes, Hum. Gene Ther., 14(14):1287-1296 (2003).
Koldej, R. et al., Optimisation of a multipartite human immunodeficiency virus based vector system; control of virus infectivity and large-scale production, J. Gene Med., 7:1390-1399 (2005).
Kudora, H. et al., Simplified lentivirus vector production in protein-free media using polyethylenimine-mediated transfection, J. Virol. Methods, 157(2):113-121 (2009).
Lennaertz, A. et al., Viral vector production in the integrityi:ID iCELLis@ single-use fixed-bed bioreactor, from bench-scale to industrial scale, BMC Proceedings, 7(Suppl 6):59-60 (2013).
Lesch, H. P. et al, Process Development of Adenoviral Vector Production in Fixed Bed Bioreactor: From Bench to Commercial Seale, Human Gene Therapy, 26(8): 560-571 (2015).
Liu, H. et al., A high-yield and scaleable adenovirns vector production process based on high density perit1sion culture of HEK 293 cells as suspended aggregates, J. Biosci. Bioeng, 107(5):524-9 (2009).
Meuwly, F. et al., Packed-bed bioreactors for mammalian cell culture: bioprocess and biomedical applications, Biotechnol Adv., 25(1):45-56 (2007).
Naldini, L. et al., Efficient transfer, integration, and sustained long-term expression of the transgene in adult rat brains injected with a lentiviral vector, Proc. Natl. Acad. Sci., 93:11382-11388 (1996).
Petiot, E. et al., Influence of HEK293 metabolism on the production of viral vectors and vaccine, Vaccine, 33(44):5974-81 (2015).
Rajendran, R. et al., Assessment of packed bed bioreactor systems in the production of viral vaccines, AMB Express, 4:25 (2014).
Reiser, J., Production and concentration of pseudotyped HIV-I-based gene transfer vectors, Gene Ther., 7:910-913 (2000).
Rodrigues, A. F. et al., Retroviral vector production under serum deprivation: The role of lipids, Biotechnol Bioeng., 104(6):1171-81 (2009).
Segura, M. M. et al., Production oflentiviral vectors by large-scale transient transfection of suspension cultures and affinity chromatography purification, Biotechnol. Bioeng., 98(4):789-799 (2007).
Seifert, G. K. E. and Matteau, P. P., An Automatic Aseptic Bioreactor Sampling System, Biotechnology and Bioengineering, 32:923-926 (1988).
Sena-Esteves, M. et al., Optimized large-scale production of high titer lentivirus vector pseudotypes., J. Virol. Methods, 122(2):131-139 (2004).
Slepushkin,V. et al., Large-scale Purification of a Lentiviral Vector by Size Exclusion Chromatography or Mustang Q Ion Exchange Capsule, BioProcessing Journal 2:89-95 (2003).
Tiscornia, G. et al., Production and purification of lentiviral vectors, Nat. Protoc., 1:241-245. (2006).
Vellinga, J. et al., Challenges in Manufacturing Adenoviral Vectros for Global Vaccine Product Deployment, Human Gene Therapy, 25:318-327 (2014).
Wang, X. et al., Large-scale Clinical-grade Retroviral Vector Production in a Fixed-Bed Bioreactor., J. Immunother., 38(3):127-135 (2015).
Written Opinion for PCT/IB2017/001205, 7 pages (dated Nov. 29, 2017).
Written Opinion for PCT/US2017/025681, 13 pages (dated Oct. 2, 2017).
Wu, S. C. et al., Production ofretrovirus and adenovirus vectors for gene therapy: a comparative study using microcanier and stationary cell culture, Biotechnol Prog., 18(3):617-22 (2002).
Drouin, H., Increasing the Performance of Mammalian Perfusion Culture System, A thesis submitted in partial fulfillment of the requirement for the degree of doctor of philosophy, The University of British Columbia, 170 pages (2010).

* cited by examiner

LARGE-SCALE PEI-MEDIATED PLASMID TRANSFECTION

RELATED APPLICATIONS

This application is the National Stage of International Application PCT/IB2017/001205, filed Apr. 24, 2017, which asserts priority to International Application PCT/US2017/025681, filed Apr. 3, 2017, which claims the benefit of U.S. Provisional Application No. 62/322,651, filed Apr. 14, 2016, and the contents of all of which are herein incorporated by reference in their entirety.

GOVERNMENT INTEREST

None

PRIOR DISCLOSURES

Note applicable.

BACKGROUND

Many vectors used in gene therapy, such as Lentiviral vectors and Adeno-associated Virus (AAV) are commonly produced by co-transfecting adherent HEK 293T cells with several different plasmid constructs (Follenzi and Naldini, 2002; Tiscornia et al., 2006; Chiorine et al. 1999). The most commonly used reagent in plasmid transfection is calcium phosphate (Tiscornia et al., 2006; Follenzi and Naldini, 2002; Reiser, 2000; Koldej et al., 2005; Naldini et al., 1996a; Sena-Esteves et al., 2004). Alternatively other reagents, like an activated dendrimer-based SUPERFECT™ (Coleman et al., 2003) or N,N-bis (2-hydroxyethyl)-2-aminoethanesulfonic acid (BES) (Karolewski et al., 2003), have been used. Polyethylenimine ("PEI") mediated transfection has also gained interest (Kuroda et al., 2008, Segura et al 2007, Chahal et al. 2014).

Many applications have still relied on flask type two dimensional (2D) approaches such as Cell Factory™. Production up-scaling in flasks is limited by the production space required and multiple units makes it impractical to handle and difficult to monitor/control culture conditions. Microcarriers have also been tried (Wu et al., 2002), dispersed in suspension but have not proven easy enough to handle to ensure homogenous growth. A critical limitation has been the expansion of large cell mass on a static vessel, a process with limited scalability. This approach also needs labor-consuming operations for the separation and purification of the vector from the producer cells later in the process. (Dormond et al., 2009).

The use of packed-bed bioreactors have provided three dimensional (3D) controlled, perfusable systems with low shear stress for adherent (and suspension) cells (Meuwly et al., 2007). A novel fixed-bed bioreactor, the iCELLis® provides a recent development providing from 66 $m^2$ to 500 $m^2$ of a polyethylene terephthalate (PET) matrix substrate for adherent cell growth (FIG. 1). (N.B.: In our patent, we use the term "substrate" not in the enzymology sense of a compound which is changed by an enzyme, but in the cell culture sense of a material providing a solid surface to which cells can adhere and grow in adherent mode, for example a polymer matrix or other macrocarrier) The iCELLis® Nano has been used for a range of vector applications, such as for AAV (Lennaertz et al., 2013), retrovirus (Wang et al., 2015), Rabies, Hepatitis-A and Chikungunya vaccine production (Rajendran et al., 2014). Previously, we evaluated for the first time the fixed bed iCELLis® bioreactor for the manufacturing of Ad5 vectors in a HEK293 cell line (Lesch et al. 2015). The process development was started in an iCELLis® Nano and for the first time we achieved efficient scale up of the manufacturing into iCELLis® 500 large scale equipment. A surprising finding at the time was to use suspension techniques to expand the cell mass for adherent bioreactor where the cells attached onto the macrocarriers and continued the growth in an adherent more (Patent number GB14/17042.7 and PCT.US2015.46927). By using this approach iCELLis® 500 can provide up to 500 $m^2$ of cell culture area in adherent mode to meet the good manufacturing practices (GMP) requirements for the manufacturing of commercial scale product.

Even though several suspension approaches are available for many viruses (Kamen et al., 2004, Ferreira et al., 2005, Cortin et al. 2004, Liu et al., 2009), the adherent HEK293 or HEK293T cell line is often crucial because the productivity of the specific vector in adherent mode can be much higher than in suspension. The use of FBS may not be a desired trend, but in some occasion, the addition of FBS was needed to increase the productivity and is thus essential. This phenomenon has seen previously with adenovirus (Iyer et al., 1999) and other virus types, especially with enveloped viruses. For example, the lipids were shown to be a key serum component during retroviral vector production to increase the yield and vector stability (Rodrigues et al. 2009). Understanding the cell metabolism and the deprivation of serum or replacing it with synthetic molecules are constantly increasing area of interest (Petiot et al., 2015). In addition, there are some cell lines that cannot be grown is suspension mode, so adherent systems are the only possibility.

The need for large scale adherent manufacturing is clear. The iCELLis® fixed-bed bioreactor with 3D PET matrix provides homogenous media control and an effective headspace gassing system. The system provides a Single Use System ("SUS") comprising a readily disposable cassette housing the PET adherent culture substrate, combined with medium perfusion capability and with automated control of stirring, temperature, pH and dissolved oxygen, which it can minimize batch-to-batch variation. We tested the iCELLis® fixed bed bioreactor and optimized it for adenovirus production in a small scale and then scaled up into a large scale 100 $m^2$ bioreactor (Lesch et al 2015). The iCELLis® 500 provides the process in a disposable manner with all probes and tubing delivered sterile and disposable. This is highly desirable for GMP manufacturing, as with disposable systems, there are no regulatory requirements to validate the product specific equipment cleaning or sterilization. The preparation of the equipment was fast and the risk of contamination was minimized with the closed system transfers. It was easy to set up and use.

Transient transfection method in a small scale is straightforward to perform, versatile and avoids the time-consuming development of stable cells lines. It also allows easy and rapid testing of various transgenes or pseudotypes (Sena-Esteves et al., 2004). Adherent large scale production with plasmid transfection has been achieved using 10 layer Cell Factory™ (Geraerts et al., 2005; Slepushkin et al., 2003). The scalability of any flask type approach, however, is limited. Also, the scalability of the transfection itself may become a challenge. We have recently figured out how to use an iCELLis®-type bioreactor for manufacturing of lentivirus and AAV using calcium phosphate- or PEI-mediated plasmid transfection-based production system (FIG. 1). We found that a constant pH, automatically provided in commercially-available bioreactors, if used during the transfection may markedly decrease transfection efficiency (GB14/17042.7 and PCT.US2015.46927). Since then we have found other counter-intuitive ways to improve PEI-mediated transfection.

We have optimized PEI mediated transfection by finding several new approaches to constructing the plasmid DNA and PEI complex. Our research has revealed that several experimental variables are results-critical. These results-critical variables include mixing time, incubation time, DNA concentration and pH control. Our findings are surprising because the art does not teach, nor even imply, that any of these variables is significant in large-scale PEI-mediated transfection in limited volume.

DESCRIPTION

The manufacturer of PEIpro® (Polyplus transfection) recommends the use of PEI at 1-6 μl of PEIpro® per μg of DNA for HEK293 cells. For adherent cells, the recommended amount of DNA is 0.1-0.58 μg/cm2, depending of the type of the flask when the total concentration is up to 0.029 μg/μl (Polyplus, PEIpro® in vitro DNA transfection reagent protocol).

Figure 3:
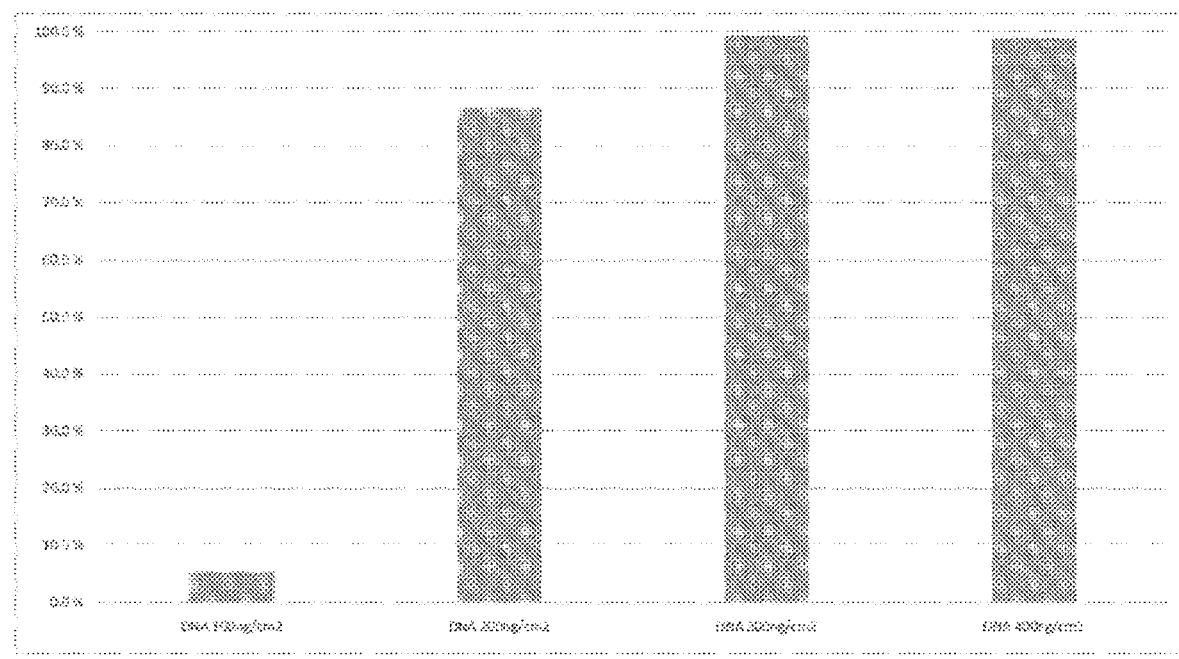
FIG. 3 shows results from our initial testing of PEI-mediated transfection only by using one plasmid and PEIpro® transfection reagent in flasks by following the manufacturer's instructions, in an iCELLis® bioreactor.
Figure 4:
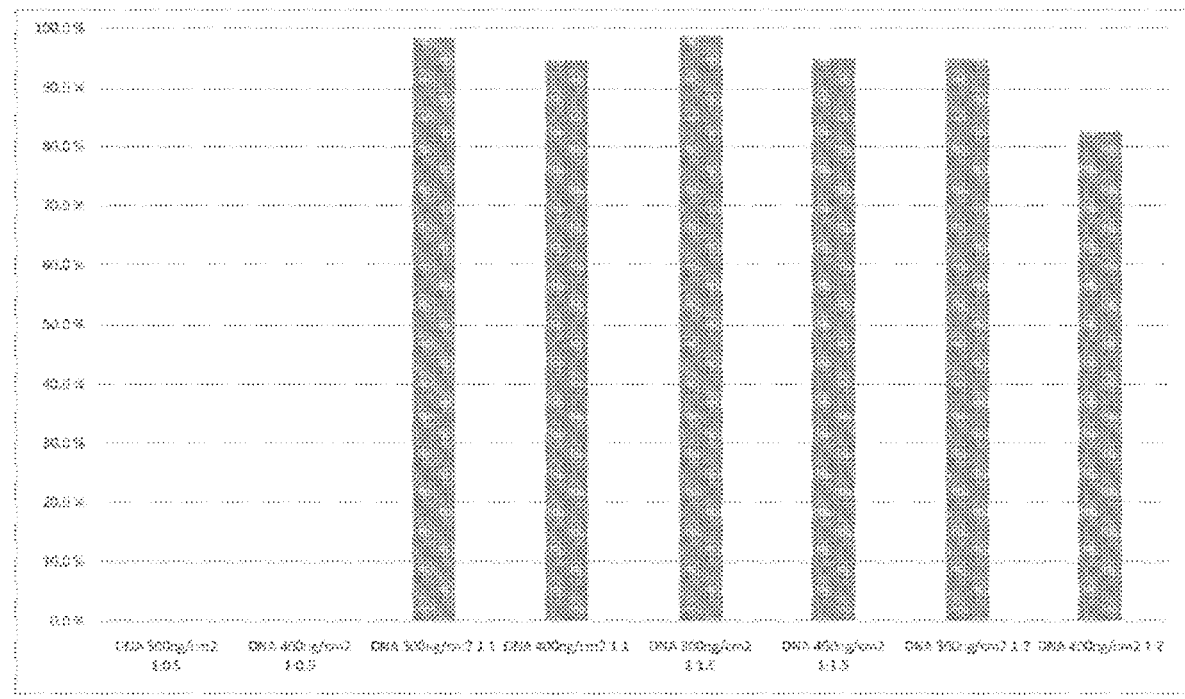
FIG. 4 shows the DNA concentration in our transfection mix (i.e., the plasmid DNA mixed with PEI, before adding that mixture to the host cells).

First we did "as instructed" by the art in a small scale. A problem came when we tried to scale that up, however, because we realized that the art-recommended approach does not work in a large scale where the working volume is limited. We initially tested PEI mediated transfection only by using one plasmid and PEIpro® transfection reagent in flasks by following the manufacturer's instructions (FIG. 3). We used a DNA amount from 100 to 400 ng/cm$^2$, evaluated using a DNA:PEI ratio of 1:1. Results showed that 300-400 ng/cm$^2$ total DNA concentration achieved the highest transfection efficiency (up to 98% positive cells) in our cells. The DNA concentration in our transfection mix (i.e., the plasmid DNA mixed with PEI, before adding that mixture to the host cells) we evaluates was up to 15 μg/ml. Also, we used different PEI ratios, and found that the PEI ratio has an effect on the transfection efficacy (FIG. 4). We found that the best transfection efficacy was achieved by using PEI:DNA ratio of about 1:1.5.

In our next experiments, the total DNA concentrations per cm$^2$ were the same, but we used DNA which contained four different plasmids, as is typically used for retroviral vector production. Virus production by producer cells which have been transfected with several plasmids is tricky because the producer cells require a larger volume of plasmid DNA (i.e., several different plasmid constructs) than a typical recombinant protein production where only one plasmid is used to express the one polypeptide of interest. We found that the highest titers were achieved using the best conditions shown in a previous experiments.

The first PEI mediated plasmid transfection in an iCELLis® bioreactor was done by Lennaertz et al. when they produced AAV in a 0.53 m$^2$ fixed-bed bioreactor. Their results showed that plasmid transfection is feasible in the low bed height laboratory-scale iCELLis® nano bioreactor (Lennaertz et al., 2013).

Figure 1:
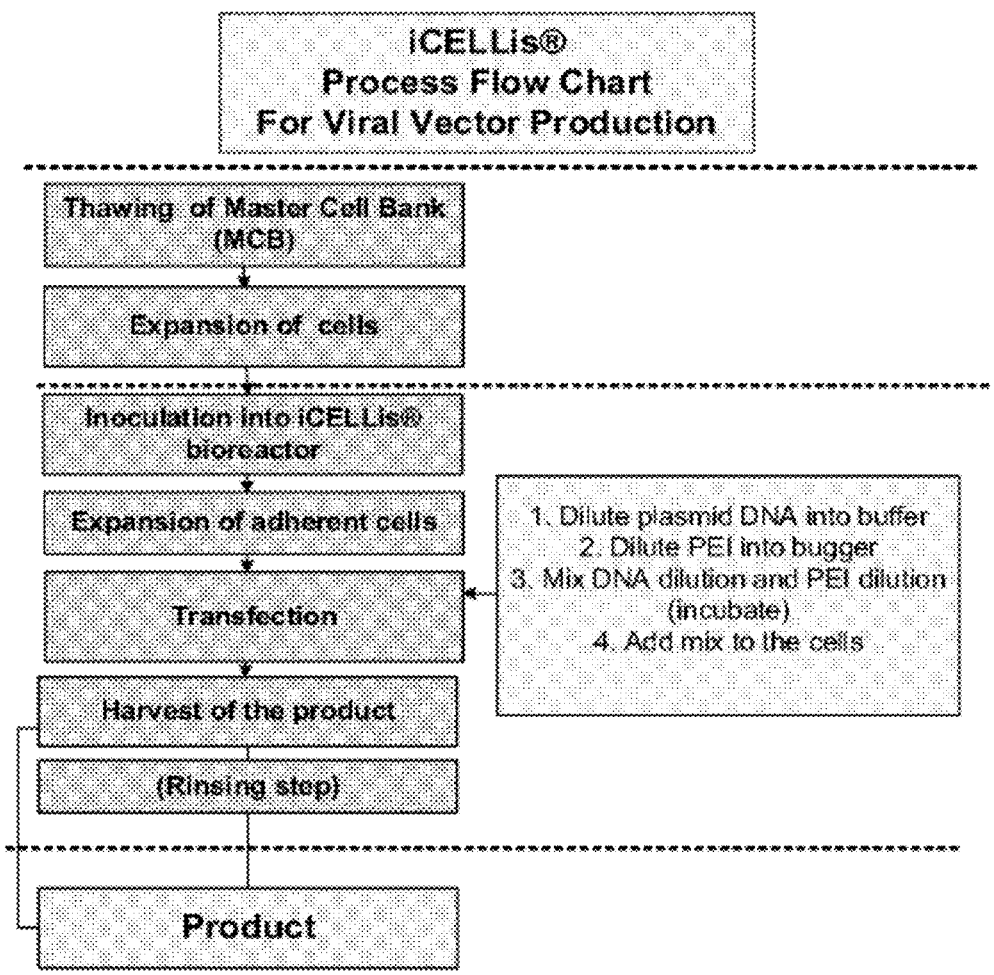
FIG. 1 is a flow-chart of the process steps for using PEI in a novel fixed-bed bioreactor, the iCELLis® bioreactor.

Our next aim was to test virus production using iCELLis® fixed bed bioreactor with the same conditions than in flasks (manufacturer's instructions) but this time using the largest 4 m$^2$ iCELLis® Nano bioreactor (fixed-bed comparable for 500 m$^2$ in iCELLis® 500) (FIG. 1). It was surprisingly observed that actually the recommended transfection conditions are not scalable and applicable for iCELLis® bioreactors, especially in higher bed height (>2 cm) bioreactors due to its limited working volume for high total cell number if the DNA amount would have been kept the same per cell or per cm$^2$. In other words, if the same plasmid transfection mix would have been used, it would not fit into the bioreactor or would have required full medium exchange during the transfection. The iCELLis® Nano is a small scale equipment where the full medium exchange can be done fast and is not limiting step in a process. In contrast, the iCELLis® 500 at scale, the full medium exchange is not practical process step because it takes time and may be influencing on cell viability due to the fact that during the draining, stirring is closed and the cells on the upper carriers are without the medium. Thus there was a need to decrease the volume in transfection mix which lead to higher DNA (plasmid) concentration in a mix but transfection efficacy was decreased (Run 1, table 1). We were able to avoid formation of aggregation by continuous mixing of the DNA-PEI mix before adding to the cells or with shorter incubation time (table 1). If we would have kept the DNA concentration the same in a iCELLis® nano than in flasks, total of 800 ml transfection mix would have needed which is the maximal working volume in the iCELLis® nano scale. Alternatively, recirculation is required in iCELLis® fixed bed bioreactor when the ≥4 cm bed height is used. In 2 cm fixed bed, lower cell amount do not require that much plasmids (transfection mix) and thus the bioreactor volume is not limiting factor. Thus Lennaertzt et all. did not face any problems in their transfection (Lennaertz et al 2013). We tested the transfection by making plasmid-PEI mix in a large volume (lower concentration), and adding it to the bioreactor but because the bioreactor working volume was exceeded, we used a re-circulation loop (FIG. 2) (run 7, table 1).

Another surprise was seen during the large scale transfection. After adding transfection mix into the bioreactor, everything seem to be normal but when sampling the bioreactor, chemical reaction was observed when normal shape plasmid tube "collapsed" or "melted" because of the medium sample with transfection mix. It was find out that PEI could react with $CO_2$. Based on all what happened and what was seen, it was concluded that $CO_2$ flow (pH control) should be shut down to be able to avoid any chemical reaction in a bioreactor. This can be a major safety aspect too.

We have found several ways to optimize the large scale plasmid transfection to produce high titer viral vectors (or any other biological product) in bioreactors (such as, but not limited to, the iCELLis® fixed bed bioreactor). We have also found a way to improve the safety of the PEI-based production by controlling $CO_2$ flow during the transfection, and short incubation of the transfection mix (DNA-PEI). When (plasmid) DNA is mixed to the transfection reagent, we have found that there is several factors not previously known to influence influencing on the transfection efficiency do in fact have results-critical effect when transfection is attempted at scale. These factors are:
1. Plasmid DNA concentration
2. PEI to plasmid DNA ratio
3. Incubation time
4. Mixing during the precipitation
5. Temperature
6. Medium
7. pH The most optimal conditions may not be practical to perform in large scale to transduce cells in a bioreactor where a high cell density is in relative limited volume. If there is a need to decrease the volume of the transfection mix, increased plasmid DNA concentration may not accomplish optimal DNA-PEI precipitation, and may lead even to DNA aggregation, rendering the DNA in a physical aggregate physically too large to properly transfect a host cell. To prevent aggregation, we surprisingly have found that a shorter transfection mix incubation time before adding the mix to the cells is preferable. This finding was surprising and counter-intuitive because the art teaches that to increase transfection, one should increase the time the plasmid is incubated with the transfection reagent to 20 min.

Continuous Mixing of the Transfection Mix (DNA-PEI) Prior Addition to the Cells

Similarly, the conventional practice in the art is to combine the plasmid DNA and the transfection reagent, and allow the combination to rest, allowing precipitation, because stirring is thought to interfere with precipitation forming, perhaps by physically moving plasmid DNA away from a transfection reagent. We found that when performed at scale, allowing the mixture to sit tranquil is in fact disadvantageous, and the combination should be stirred or mixed during the incubation time, preferably stirred or mixed for substantially the entire transfection incubation time.

Figure 5:
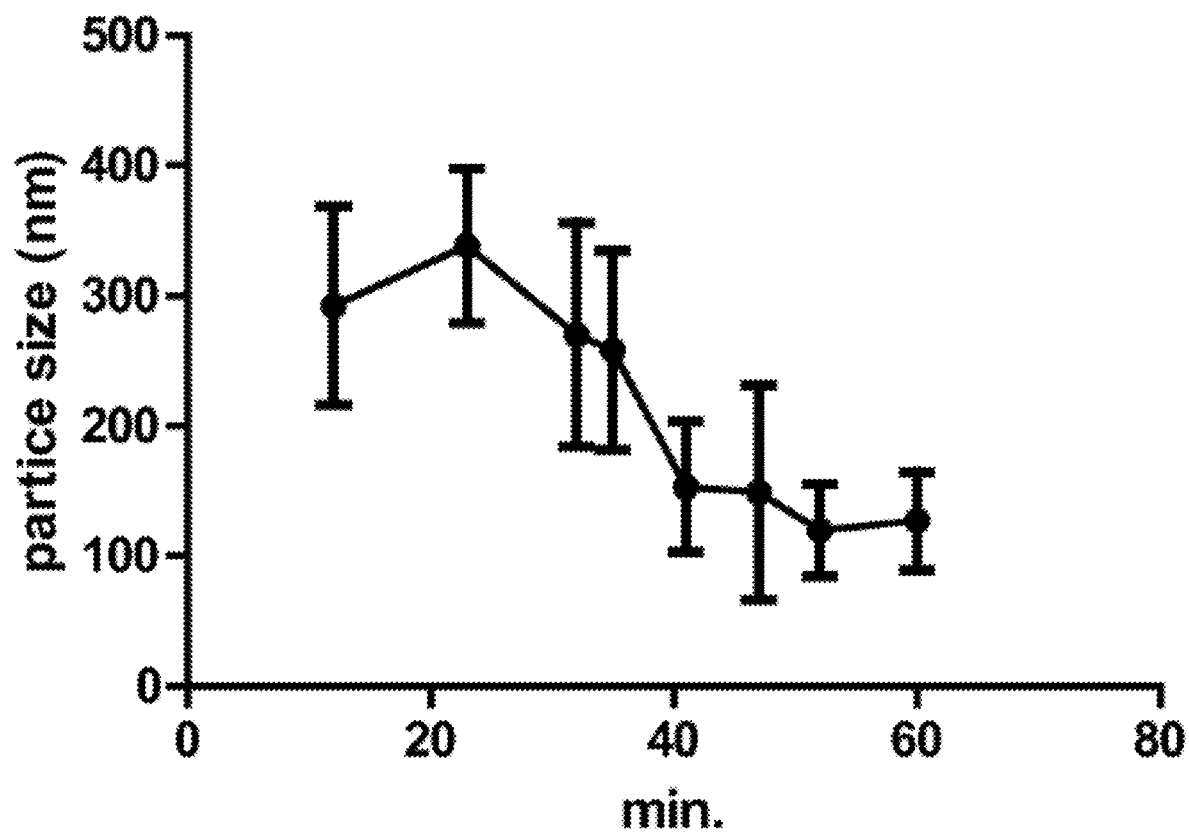
FIG. 5 shows the effect of prolonged incubation (by mixing) on DNA-plasmid particle size.

Continuous Mixing and Prolonged Incubation of the Transfection Mix (DNA-PEI) Prior Addition to the Cells Similarly, the art teaches precipitation is substantially complete within about 20 minutes, so one should add the mixture to the cells at 20 minutes. Alternatively, we found that when performed at scale, DNA-PEI complex formation depends on the relative concentration of each, and the concentration of both in the medium. We thus surprisingly found that when performed at scale, may continue for longer than twenty minutes, so transfection at scale may require a materially longer incubation than the 20 minute period recommended by the prior art. To avoid the aggregation, it is preferred to stir or mix the transfection mix during the incubation time. It was also observed that prolonging incubation time has an effect on DNA/PEI particle size formation. It was observed that prolonged incubation (by mixing) is increasing the particle size until 35 min, but decreasing the size after that (FIG. 5).

Increasing the transfection volume can be overcome by adding the transfection mix to recirculation loop.

Figure 2:
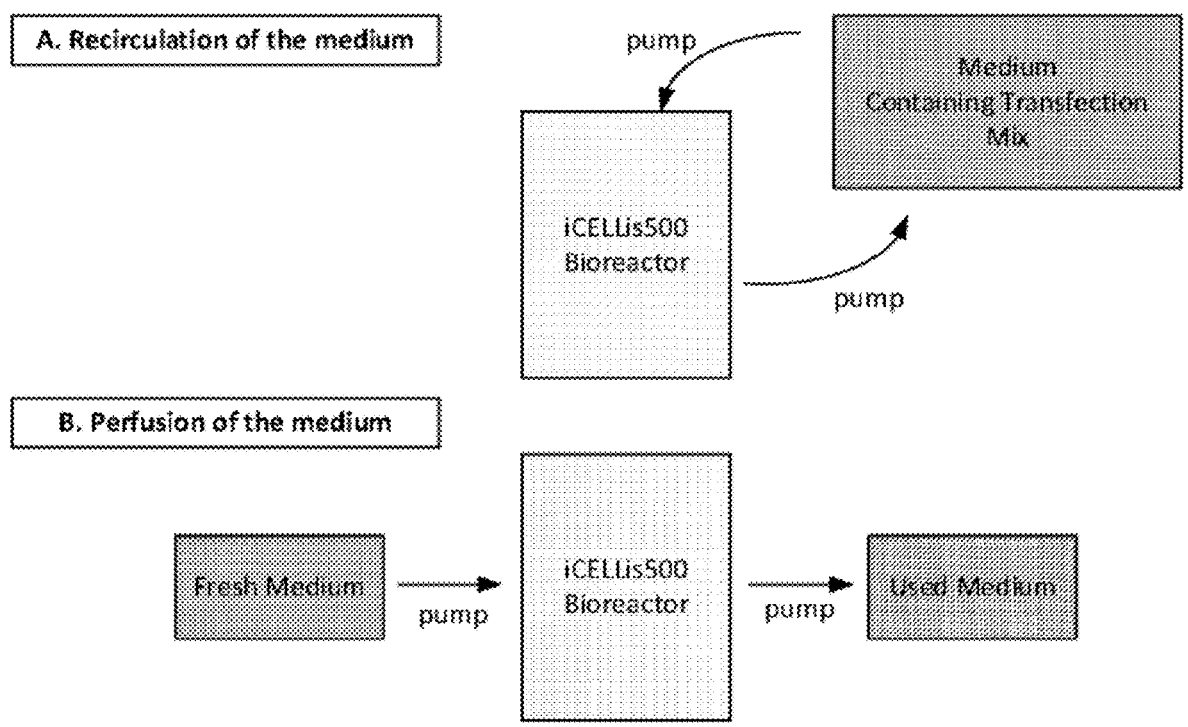
FIG. 2 is a flow-chart of the process steps for media exchange in a novel fixed-bed bioreactor, the iCELLis® bioreactor.

As mentioned above, the art suggests that increased DNA concentration can lead to DNA aggregation, rendering the DNA unavailable for transfection. The art teaches to reduce DNA concentration by perfusion, in effect washing DNA out of the transfection vessel entirely. This works, but it wastes a tremendous amount of plasmid. We surprisingly found a way that one can transfect at scale and overcome the limited volume issue of excessive DNA concentration by re-circulation of the transfection mix and culture medium during the transfection (FIG. 2). This finding was counter-intuitive because the art suggested that re-circulating the culture medium would re-circulate an excess amount of DNA into the transfection vessel. This way the volume of DNA-PEI can be increased, lowering the actual concentration of DNA-PEI during the mixing/incubation time and also after adding the mix to the bioreactor.

We tested the transfection using the 200 ml volume when the full medium enhanced was not required. This way the DNA concentration in a mix increased from 0,015 µg/µl to 0.05 µg/µl. When the PEI was mixed with plasmid, and incubated 15-20 min. at room temperature according to the manufacturer, remarkable visible DNA aggregation was observed. Typically plasmids and PEI should form opal or "cloudy" homogenous precipitation to be able to efficiently transfect the cells. In our case, visual large plasmid aggregation was formed during the incubation. Also transfection efficiency was surprisingly low (40%, measured by sampling the upper carriers from the fixed bed), and productivity decreased. Even though mix should be incubated to allow the DNA and PEI to form a cloudy precipitation, our next experiment was done by limiting the incubation time (<10 min.) when less problematic "too large" aggregation was formed. This improved transfection efficiency. Also we tested the volume increase by doubling the volume of transfection mix into 480 ml when the concentration of the DNA was decreased.

The transfection reagent can be PEIpro® (PolyPlus), jetPEI®, linear PEI or any polyethylene imine derivative. It may also be any other functionally-equivalent transfection reagent.

EXAMPLES

Plasmid Transfection

We tested the transfection using the 200 ml volume when the full medium enhanced was not required. This way the DNA concentration in a mix increased from 0,015 µg/µl to 0.05 µg/µl. When the PEI was mixed with plasmid, and incubated 15-20 min. at room temperature according to the manufacturer, remarkable visible DNA aggregation was observed (Table 1). Typically, plasmids and PEI should form opal or "cloudy" homogenous precipitation to be able to efficiently transfect the cells. In our case, visual large plasmid aggregation was formed during the incubation. Also, transfection efficiency was surprisingly low (40%, measured by sampling the upper carriers from the fixed bed), and productivity decreased. Even though mix should be incubated to allow the DNA and PEI to form a cloudy precipitation, our next experiment was done by limiting the incubation time (<10 min.) when less problematic "too large" aggregation was formed. This improved transfection efficiency. Also we tested the volume increase by doubling the volume of transfection mix into 480 ml when the concentration of the DNA was decreased. Best transfection efficacy was achieved when DNA concentration was further increased and DNA-PEI mix as incubated for 7.5 minutes with mixing, before addition to the bioreactor (Table 1).

First we tested PEI mediated transfection only by using one plasmid and PEIpro® transfection reagent in flasks by following the manufacturer's instructions (FIG. 3). We used a DNA amount from 100 to 400 ng/cm$^2$, evaluated using a DNA:PEI ratio of 1:1. Results showed that 300-400 ng/cm$^2$ total DNA concentration achieved the highest transfection efficiency (up to 98% positive cells) in our cells. The DNA concentration in our transfection mix (i.e., the plasmid DNA mixed with PEI, before adding that mixture to the host cells) we evaluates was up to 15 μg/ml. Also, we used different PEI ratios, and found that the PEI ratio has an effect on the transfection efficacy (FIG. 4). We found that the best transfection efficacy was achieved by using PEI:DNA ratio of about 1:1.5.

In our next experiments, the total DNA concentrations per $cm^2$ were the same, but we used DNA which contained four different plasmids, as is typically used for retroviral vector production. Virus production by producer cells which have been transfected with several plasmids is tricky because the producer cells require a larger volume of plasmid DNA (i.e., several different plasmid constructs) than a typical recombinant protein production where only one plasmid is used to express the one polypeptide of interest. We found that the highest titers were achieved using the best conditions shown in a previous experiments (data not shown).

The next aim was to test virus production using iCELLis® fixed bed bioreactor with the same conditions but this time using the largest 4 $m^2$ iCELLis® Nano bioreactor (fixed-bed comparable for 500 $m^2$ in iCELLis® 500). It was observed that actually the recommended transfection conditions are not scalable and applicable for iCELLis® bioreactors, especially in a higher bed height (>2 cm) bioreactors due to its limited working volume for high total cell number if the DNA amount would have been kept the same per cell or per $cm^2$. In other words, if the same plasmid transfection mix would have been used, it would not fit into the bioreactor, or would have required a full medium exchange during the transfection. The iCELLis® Nano is a small-scale equipment where the full medium exchange can be done fast and is not limiting step in a process. In contrast, at the scale of an iCELLis® 500 the full medium exchange is not a practical process step because it takes time and may influence cell viability due to the fact that during the draining, stirring is closed and the cells on the upper carriers are without the medium. Thus, there was a need to decrease the volume in transfection which lead to higher DNA (plasmid) concentration in a mix. If we would have kept the DNA concentration the same, total of 800 ml transfection mix would have needed which is the maximal working volume. Thus, we tested the transfection using the 200 ml volume when the full medium enhanced was not required. This way the DNA concertation in a mix increased from 0.015 μg/μl to 0.05 μg/μl. When the PEI was mixed with plasmid, and incubated 15-20 minutes at room temperature according to the manufacturer's instructions, remarkable visible DNA aggregation was observed. Typically plasmids and PEI should form an opalescent or "cloudy" homogenous precipitation to be able to efficiently transfect the cells. In our case, however, visual large plasmid aggregation was formed during the incubation. Also, transfection efficiency was surprisingly low (40%, measured by sampling the upper carriers from the fixed bed), and productivity decreased. Even though mix should be incubated to allow the DNA and PEI to form a cloudy precipitation, our next experiment was done by limiting the incubation time (<10 min.) when less problematic "too large" aggregation was formed. This improved transfection efficiency. Also we tested the volume increase by doubling the volume of transfection mix into 480 ml when the concentration of the DNA was decreased.

Improvement for the situations was get when transfection mix was stirred also during the incubation. We concluded that the stirring during the incubation is actually prohibiting the large aggregation when the precipitated molecules are still in reasonable small size and no large aggregation can be formed. The formation of the precipitation was followed by Nanosight™ when the size variation and number of particle can be monitored based on brown movement. Our invention is against the common knowledge that when large transfection is done, the continuous mixing is required or additional the stand-still incubation needs to be shorten than recommended (<20 min).

pH Control

Bioreactors are typically provided with an automatic pH control to maintain the culture medium at a constant pH, automatically adding a basic solution (e.g., a sodium bicarbonate solution) if the culture medium pH falls. We have previously shown (patent number GB 14/17042. 7) that during the transfection if the automatic pH control in the iCELLis® bioreactor is left operational, then the bioreactor will add base solution into the bioreactor, which will cause the formation of a precipitate in the bioreactor. With calcium phosphate transfection, the precipitate, which we believe is a DNA-salt precipitate, is undesirable because it clogs the bioreactor and impedes productivity. We found that by disabling the automatic pH control during (before or just after) the transfection and allowing the pH of the culture medium to fall naturally, the resulting slightly-acidic culture medium prevents precipitate formation and thus increases yield. We here made same observation also with PEI based transfection that there is a need to switch-off the pH control because during the transfection, the system is automatic adding base into the bioreactor and locally this may cause high pH change and lead to either aggregation or detaching of DNA or PEI from the complex.

Re-Circulation Mode

To find the optimal conditions for large-scale transfection, we also tested re-circulation method when the bioreactor was equipped with recirculation instead of perfusion during transfection. With recirculation loop, half of the transfection mixture was added to the bioreactor and the other half to the recirculating medium until the total volume was 1000 ml, and the mixture was added to the bioreactor by recirculating the transfection mixture through the bioreactor. The recirculation loop was replaced with perfusion 24 h post-transfection ("PT"). Critical was to switch of the pH control. Transfection efficacy was comparable, but that might not as practical to perform and requires increased amounts of medium (Table 1, run 7).

Safety Improvement by Switching of $CO_2$

Another surprise was seen during the large scale transfection. Transfection mix containing DNA, PEI and medium without FBS was done. Base and DO controls as well as perfusion were OFF during transfection, but $CO_2$ control was ON. Everything seemed to working, and the values on the screen of the iCELLis® were as they were supposed to be. Anything else unusual was not noticed at that point. A 5 ml sample was taken from the bioreactor at 14:00 into a 15 ml Falcon tube for glucose and lactate measurements. Before the sample was taken, the tube was normally shaped. After taking the sample, the operator who took the sample was holding the tube, while emptying the sample bottle back into the bioreactor. After 2-3 min the operator viewed the tube that contained the sample and surprisingly found that the tube had changed its form. It was collapsed/flattened, but no scratches were visible. Later, also a plastic Erlenmeyer flask containing sample from the bioreactor also appeared to be "melted" as if by excess heat. The apparent "melting," however, was not caused by the heat. It was found that PEI can react with $CO_2$ causing a chemical reaction. Based on all what happened and what was seen, it was concluded that $CO_2$ flow should be shut down to be able to avoid any chemical reaction in a bioreactor. This can be a major safety aspect, too.

TABLE I

Transfection optimization and the influence in the transfection efficacy and the total yield

| Run number | Transfection mix | Transfection efficiency | Yield |
|---|---|---|---|
| 1 | PEI and DNA 300 ng/cm$^2$ in 120 ml IMDM without serum (+glut + P/S) -> separate mixes (a'120 ml). Visual aggregation seen. Mixes in 50 ml Falcons, vortexing pairwise and pouring into glass beaker -> 15 min incubation RT without mixing | 35-40% | 4.05E+09 |
| 2 | PEI and DNA 300 ng/cm$^2$ in 240 ml medium without serum (+glut + P/S) -> separate mixes (a'240 ml) Mixes in 500 ml erlenmayer -> PEI mix was poured into DNA mix -> Mixing with magnetic stirring -> 10 min incubation RT without mixing | 43% | 2.83E+09 |
| 3 | PEI and DNA 300 ng/cm$^2$ in 240 ml mediumwithout serum (+glut + P/S) -> separate mixes (a'240 ml) Mixes in 500 ml erlenmayer -> PEI mix was poured into DNA mix -> Mixing strongly with magnetic stirring -> 10 min incubation RT without mixing | 75% | 2.09E+09 |
| 4 | PEI and DNA 300 ng/cm$^2$ in 240 mlmedium without serum (+glut + P/S) -> separate mixes (a'240 ml) Mixes in 500 ml erlenmayer -> PEI mix was poured into DNA mix -> mixing with magnetic stirring -> 5 min incubation RT mixing gently | 65-70% | 3.17E+09 |
| 5 | PEI and DNA 400 ng/cm$^2$ in 320 ml medium without serum (+glut + P/S) -> separate mixes (a'320 ml) Mixes in 500 ml and 1 liter erlenmayer -> PEI mix was poured into DNA mix -> mixing with magnetic stirring -> 7.5 min incubation RT mixing gently | 60-80% | 5.20E+09 |
| 6 | PEI and DNA 300 ng/cm$^2$ in 240 ml medium without serum (+glut + P/S) -> separate mixes (a'240 ml) Mixes in 500 ml erlenmayer -> PEI mix was poured into DNA mix -> mixing with magnetic stirring -> 5 min incubation RT mixing gently | 50-60% | 9.06E+09 |
| 7 | DNA 336 ng/cm$^2$ in 240 ml medium without serum (+glut + P/S) -> separate mixes (a'240 ml) Mixes in 500 ml erlenmayer -> PEI mix was poured into DNA mix -> mixing with magnetic stirring -> 5 min incubation RT mixing gently | NA | |

REFERENCES

Chahal P S, Schulze E, Tran R, Montes J, Kamen A A. "(2014) Production of adeno-associated virus (AAV) serotypes by transient transfection of HEK293 cell suspension cultures for gene delivery.

Chiorini J A, Kim F, Yang L, Kotin R M. (1999) Cloning and characterization of adeno-associated virus type 5.

Coleman, J. E., Huentelman, M. J., Kasparov, S., Metcalfe, B. L., Paton, J. F., Katovich, M. J., Semple-Rowland, S. L., and Raizada, M. K. (2003). Efficient large-scale production and concentration of HIV-1-based lentiviral vectors for use in vivo. Physiol Genomics 12, 221-228.

Cortin V, Thibault J, Jacob D, Garnier (2004) A. High-titer adenovirus vector production in 293S cell perfusion culture. *Biotechnol Prog.* 20(3):858-63.

Dormond E, Perrier M, Kamen A. (2009) From the first to the third generation adenoviral vector: what parameters are governing the production yield? *Biotechnol Adv.* 27(2):133-44.

Ferreira T B, Ferreira A L, Carrondo M J, Alves P M. (2005) Effect of re-feed strategies and non-ammoniagenic medium on adenovirus production at high cell densities. J Biotechnol. 119(3):272-80.

Follenzi, A. and Naldini, L. (2002). Generation of HIV-1 derived lentiviral vectors. Methods Enzymol. 346, 454-465.

Geraerts, M., Michiels, M., Baekelandt, V., Debyser, Z., and Gijsbers, R. (2005). Upscaling of lentiviral vector production by tangential flow filtration. J. Gene Med. 7, 1299-1310.

Iyer P, Ostrove J M, Vacante D. (1999) Comparison of manufacturing techniques for adenovirus production. Cytotechnology. 30(1-3):169-72.

Karolewski, B. A., Watson, D. J., Parente, M. K., and Wolfe, J. H. (2003). Comparison of transfection conditions for a lentivirus vector produced in large volumes. Hum. Gene Ther. 14, 1287-1296.

Kamen A, Henry O. (2004) Development and optimization of an adenovirus production process. J Gene Med. 6 Suppl 1:S184-S192.

Koldej, R., Cmielewski, P., Stocker, A., Parsons, D. W., and Anson, D. S. (2005). Optimisation of a multipartite human immunodeficiency virus based vector system; control of virus infectivity and large-scale production. J. Gene Med. 7, 1390-1399.

Kuroda, H., Kutner, R. H., Bazan, N. G., and Reiser, J. (2008). Simplified lentivirus vector production in protein-free media using polyethylenimine-mediated transfection. J. Virol. Methods.

Lennaertz, A., Knowles, S., Drugmand, J C., and Castillo, J. (2013) Viral vector production in the Integrity® iCELLis® single-use fixed-bed bioreactor, from bench-scale to industrial scale. 7 (Suppl 6), 59-60. 1-1-2013. BMC Proceedings.

Lesch H P, Heikkila K M, Lipponen E M, Valonen P, Müller A, Räsänen E, Tuunanen T, Hassinen M M, Parker N, Karhinen M, Shaw R, Ylä-Herttuala S. Process Development of Adenoviral Vector Production in Fixed Bed Bioreactor: From Bench to Commercial Scale.Hum Gene Ther. 2015 August; 26(8):560-71. doi: 10.1089/hum.2015.081.

Liu H, Liu X M, Li S C et al. (2009) A high-yield and scaleable adenovirus vector production process based on high density perfusion culture of HEK 293 cells as suspended aggregates. J Biosci Bioeng. 107(5):524-9.

Meuwly F, Ruffieux P A, Kadouri A, von SU. (2007) Packed-bed bioreactors for mammalian cell culture: bioprocess and biomedical applications. Biotechnol Adv. 25(1):45-56.

Naldini, L., Blomer, U., Gage, F. H., Trono, D., and Verma, I. M. (1996a). Efficient transfer, integration, and sustained long-term expression of the transgene in adult rat brains injected with a lentiviral vector. Proc. Natl. Acad. Sci. U.S.A 93, 11382-11388.

Petiot E, Cuperlovic-Culf M, Shen C F, Kamen A. (2015) Influence of HEK293 metabolism on the production of viral vectors and vaccine. Vaccine. November 4; 33(44): 5974-81.

Rajendran R, Lingala R, Vuppu S K et al. (2014) Assessment of packed bed bioreactor systems in the production of viral vaccines. AMB Express. 4:25.

Reiser, J. (2000). Production and concentration of pseudotyped HIV-1-based gene transfer vectors. Gene Ther. 7, 910-913.

Rodrigues A F, Carmo M, Alves P M, Coroadinha A S. (2009) Retroviral vector production under serum deprivation: The role of lipids. Biotechnol Bioeng. 104(6): 1171-81.

Segura, M. M., Garnier, A., Durocher, Y., Coelho, H., and Kamen, A. (2007). Production of lentiviral vectors by large-scale transient transfection of suspension cultures and affinity chromatography purification. Biotechnol. Bioeng. 98, 789-799.

Sena-Esteves, M., Tebbets, J. C., Steffens, S., Crombleholme, T., and Flake, A. W. (2004). Optimized large-scale production of high titer lentivirus vector pseudotypes. J. Virol. Methods 122, 131-139.

Slepushkin, V., Chang, N., Cohen, R., Gan, Y., Jiang, B., Deausen, D., Berlinger, D., Binder, G., Andre, K., Humeau, L., and Dropulic, B. (2003). Large-scale Purification of a Lentiviral Vector by Size Exclusion Chromatography or Mustang Q Ion Exchange Capsule. BioProcessing Journal 2, 89-95.

Tiscornia, G., Singer, O., and Verma, I. M. (2006). Production and purification of lentiviral vectors. Nat. Protoc. 1, 241-245.

Wu S C, Huang G Y, Liu J H. (2002) Production of retrovirus and adenovirus vectors for gene therapy: a comparative study using microcarrier and stationary cell culture. Biotechnol Prog. 18(3):617-22

Wang, X., Olszewska, M., Qu, J., Wasielewska, T., Bartido, S., Hermetet, G., Sadelain, M., and Riviere, I (2015) Large-scale Clinical-grade Retroviral Vector Production in a Fixed-Bed Bioreactor. 38[3], 127-135. 3-4-2015. J Immunother

We claim:

1. A method for manufacturing a recombinant lentiviral vector, the method comprising:
   (a) mixing polyethylene imine (PEI) and plasmid DNA coding for a recombinant lentiviral vector to form a transfection solution, wherein the transfection solution is incubated for longer than 20 minutes and the transfection solution is stirred or mixed throughout the incubation time such that the transfection solution does not form a DNA-PEI complex precipitate;
   (b) adding cells and the transfection solution to a bioreactor and recirculating the transfection solution until transfection is substantially complete, whereby the plasmid DNA transfects the cells to make producer cells which produce the recombinant lentiviral vector; and then
   (c) culturing the producer cells in adherent mode in the bioreactor, wherein the bioreactor has a fixed bed volume of at least 5 liters and whereby the producer cells produce the recombinant lentiviral vector; and then
   (d) harvesting recombinant lentiviral vector.

2. The method of claim 1, wherein the plasmid is present in an amount adequate to produce a PEI:plasmid DNA ratio of about 1:1.5.

3. The method of claim 1, wherein the transfection solution is at least 20 liters in volume.

4. The method of claim 1, wherein the plasmid DNA concentration in the transfection solution is at least 300 nanograms of DNA per $cm^2$.

5. The method of claim 4, wherein the plasmid DNA concentration in the transfection solution is not more than 400 nanograms of DNA per $cm^2$.

6. The method of claim 1, further comprising:
   measuring the formation of DNA-PEI complexes in the transfection solution using light scattering.

7. The method of claim 1, wherein step (b) comprises ceasing addition of $CO_2$ to the transfection solution, whereby the PEI does not react with added $CO_2$.

8. The method of claim 1, wherein the bioreactor comprises an automatic pH control mechanism, and wherein the method further comprises allowing the pH of the culture medium to fall naturally during or after transfection, producing an acidic culture medium which prevents PEI-DNA complex precipitate formation.

* * * * *